US005612364A

United States Patent [19]
York et al.

[11] Patent Number: 5,612,364
[45] Date of Patent: Mar. 18, 1997

[54] SUBSTANTIALLY PURE APRACLONIDINE

[75] Inventors: Billie M. York, Fort Worth; John M. Yanni, Burleson; Mark T. DuPriest, Fort Worth, all of Tex.

[73] Assignee: Alcon Laboratories, Inc., Fort Worth, Tex.

[21] Appl. No.: 555,252

[22] Filed: Nov. 8, 1995

[51] Int. Cl.$^6$ .................................................. A61K 31/415
[52] U.S. Cl. ...................... 514/392; 548/333.1; 514/913
[58] Field of Search .......................... 548/333.1; 514/392

[56] References Cited

U.S. PATENT DOCUMENTS 4,517,199  5/1985  York et al. ............................. 514/392
5,212,196  5/1993  House et al. .......................... 514/392

FOREIGN PATENT DOCUMENTS

WO95/21818  8/1995  WIPO.

OTHER PUBLICATIONS

Physicians' Desk Reference, Product Information, *Iopidine®*, 23rd Edition, 219–220 (1995).
Physicians' Desk Reference, Product Information, *Iopidine®* 0.5%, 23rd Edition, 219–220 (1995).

*Primary Examiner*—Patricia L. Morris
*Attorney, Agent, or Firm*—Sally Yeager

[57] ABSTRACT

Compositions containing, and methods for controlling intraocular pressure with, substantially pure apraclonidine are disclosed.

4 Claims, 1 Drawing Sheet

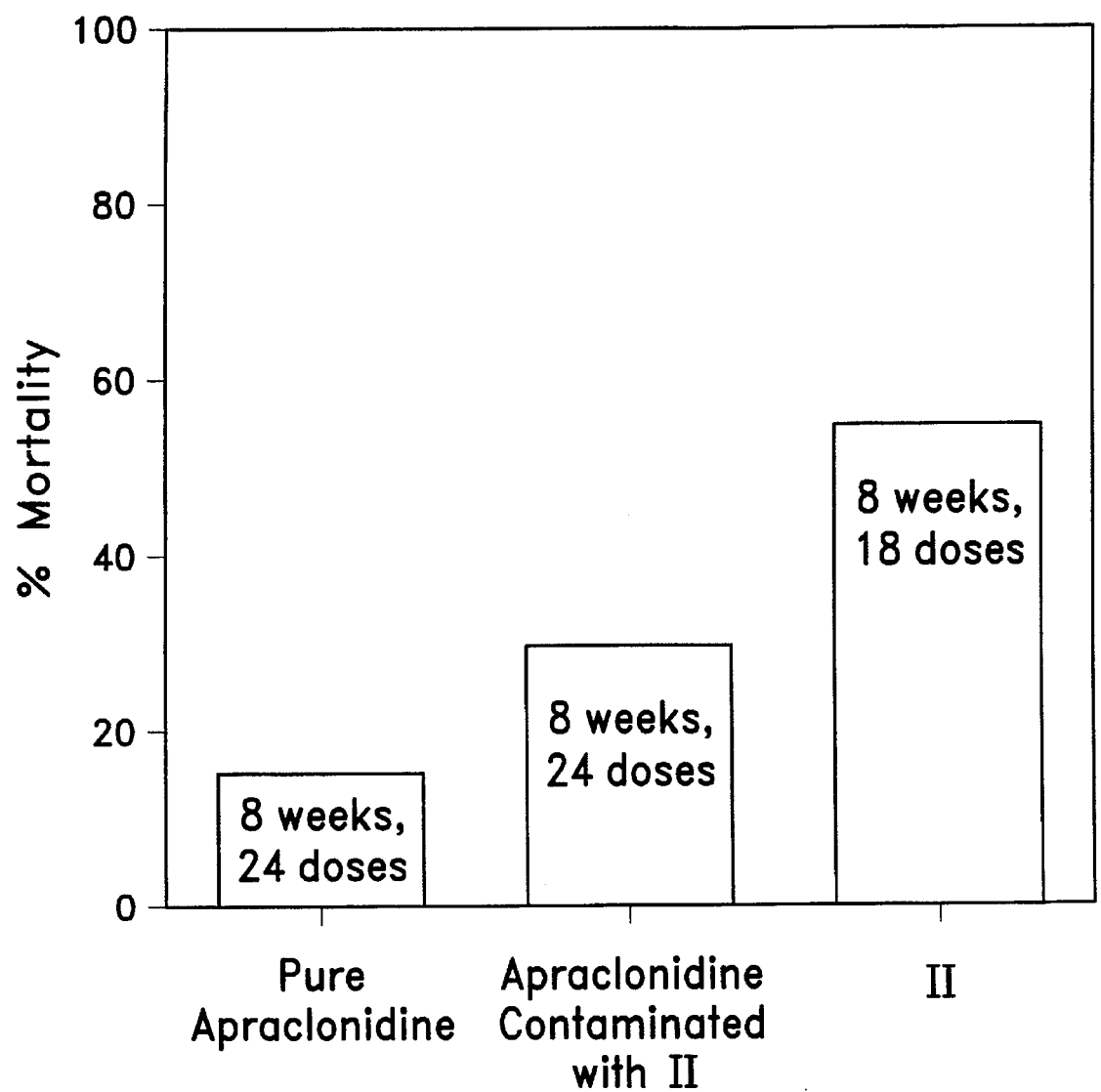

SUBSTANTIALLY PURE APRACLONIDINE

The present invention is directed to substantially pure apraclonidine and its use in lowering intraocular pressure.

BACKGROUND OF THE INVENTION

Apraclonidine (2-[(4-amino-2,6-dichlorophenyl)imino]imidazolidine monohydrochloride or para-amino clonidine) is known to be effective in lowering intraocular pressure (IOP) in persons suffering from glaucoma or ocular hypertension. See, U.S. Pat. No. 4,517,199, which is incorporated herein by reference. It is also useful in preventing IOP spikes which commonly occur during or following intraocular surgery. See, U.S. Pat. No. 5,212,196, which is incorporated herein by reference. Iopidine® 0.5% is an apraclonidine ophthalmic solution available from Alcon Laboratories, Inc., Fort Worth, Tex. It is indicated for short term adjunctive therapy in patients on maximally tolerated medical therapy who require additional IOP reduction. Iopidine® 1% is an apraclonidine solution, also available from Alcon Laboratories, Inc., indicated to control or prevent post surgical elevations in intraocular pressure. Iopidine® is contraindicated for patents with hypersensitivity to apraclonidine or any other component of the medication.

SUMMARY OF THE INVENTION

The present invention is directed to substantially pure apraclonidine and compositions thereof for controlling IOP. The invention is also concerned with methods for controlling elevated IOP, due to glaucoma, ocular hypertension, or as a result of ophthalmic surgery, by administration of the compositions to persons suffering from elevated IOP.

BRIEF DESCRIPTION OF THE DRAWING

FIG. 1 shows the mortality rate induced by chronic-topical application of pure apraclonidine, contaminated apraclonidine, and II.

DETAILED DESCRIPTION OF PREFERRED EMBODIMENTS

In the past it was believed that allergic/toxic reactions in patients administered apraclonidine (Iopidine) were due to reactions to apraclonidine itself. Surprisingly, it has been discovered that the allergic/toxic reaction is primarily due to an impurity shown below as II.

Apraclonidine has the structure:

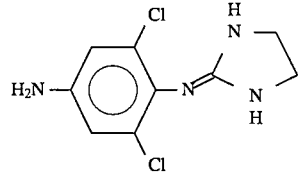

(I)

The impurity, known as (2-[(4-amino-2,3,6-trichlorophenyl)imino]imidazolidine, has the structure:

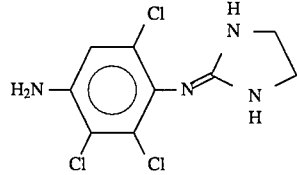

(II)

Without intending to be bound by any theory, it is believed that I and II both react with physiological nucleophiles, but that the trichloro impurity, II, is much more tissue penetrating and thus more reactive than I in covalently coupling to cell proteins and creating neoantigens which cause undesirable inflammatory responses. The advantage to using I versus apraclonidine contaminated with II is best realized in the treatment of glaucoma or ocular hypertension. Because glaucoma and ocular hypertension are chronic diseases, it is important that the pharmaceuticals being used to control the diseases have a profile which allows for their daily use for the rest of the patient's life. Any pharmaceutical that may cause inflammatory responses is not acceptable for chronic use. Substantially pure apraclonidine is acceptable for long term use.

As used herein, the term "substantially pure apraclonidine" means para-amino clonidine substantially free of (2-[(4-amino-2,3,6-trichlorophenyl)imino]imidazolidine. It can be acquired via conventional chromatography methods or through improved apraclonidine synthesis, such as disclosed in commonly owned application WO 95/21818 whose contents are incorporated herein by reference. The procedure set forth in WO 95/21818 is the preferred method for acquiring substantially pure apraclonidine.

The compositions of the present invention may contain, in addition to substantially pure apraclonidine, other ingredients typical for ophthalmic formulations. The apraclonidine may be combined with ophthalmologically acceptable preservatives, surfactants, viscosity enhancers, penetration enhancers, buffers, sodium chloride, and water to form aqueous, sterile ophthalmic suspensions or solutions. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the active ingredient in a hydrophilic base prepared from the combination of, for example, carbopol-940 or the like according to the published formulations for analogous ophthalmic preparations; preservatives and tonicity agents can also be incorporated. Ophthalmic solution formulations may be prepared by dissolving the active ingredient in a physiologically acceptable isotonic aqueous buffer. Further, the ophthalmic solution may include an ophthalmologically acceptable surfactant. Furthermore, the ophthalmic solution may contain a thickener such as hydroxymethylcellulose, hydroxyethylcellulose, hydroxypropylmethylcellulose, methylcellulose, polyvinylpyrrolidone, or the like to improve the retention of the medicament in the conjunctival sac.

The substantially pure apraclonidine is preferably formulated as a topical ophthalmic suspension or solution, with a pH of about 4.5 to 7.8. The substantially pure apraclonidine will normally be contained in these formulations in an amount of 0.1% to 10% by weight, but preferably in an amount of 0.25% to 5.0% by weight. Thus, for topical presentation, 1 to 3 drops of these formulations are delivered to the surface of the eye 1 to 4 times a day according to the routine discretion of a skilled clinician.

EXAMPLE 1

| Ingredient | % w/v |
| --- | --- |
| Substantially Pure Apraclonidine Hydrochloride | 0.5 (as base) |
| Sodium Acetate, trihydrate | 0.07 |
| Sodium Chloride | 0.757 |
| Benzalkonium Chloride | 0.01 |
| Hydrochloric Acid | Adjust pH to 5.3 |

| Ingredient | % w/v |
|---|---|
| and/or Sodium Hydroxide | |
| Purified Water | QS 100 mL |

EXAMPLE 2

| Ingredient | % w/v |
|---|---|
| Substantially Pure Apraclonidine Hydrochloride | 1.0 (as base) |
| Sodium Acetate, trihydrate | 0.07 |
| Sodium Chloride | 0.757 |
| Benzalkonium Chloride | 0.01 |
| Hydrochloric Acid and/or Sodium Hydroxide | Adjust pH to 5.3 |
| Purified Water | QS 100 mL |

The above composition is suitable for lowering and controlling the IOP spike associated with ophthalmic surgery.

EXAMPLE 3

Contact Hypersensitivity in Mice

Sensitization Method

Mice were depilated using Nair® in the morning of day 1. On day 1, 2 and 3 of week 1 10 μl of contaminated apraclonidine (apraclonidine contaminated with II), substantially pure apraclonidine, or oxazolone was applied to the abdomen of each mouse using an Eppendorf repeating pipet and a 0.5 mL capacity Eppendorf combitip. The compound was massaged into the abdomen using the side of the combitip. For week 2 to 8 the mice were depilated on each Monday morning. The compound was applied to the abdomen on Monday afternoon, Wednesday morning and Thursday afternoon of each week for a total of 24 exposures over the 8 weeks.

Challenge Procedure

Following a 1 week rest period without exposure, the mice were anesthetized using Halothane® and 5 μl of the appropriate compound was applied to each side of one ear only. Twenty-four hours later the mice were euthanized by $CO_2$, both ears removed at the base and weighed. The non-challenged ear served as a control for each mouse. An increase in weight compared to the non-challenged ear represents a positive hypersensitivity response. Statistical comparisons were performed using Paired-T test. A summary of the data is shown in the table below.

| Sensatization Agent | Challenge Agent | Δ (mg) [Controlled ear - Challenged ear] |
|---|---|---|
| 0.5% contaminated apraclonidine | Acetone (vehicle) | −2 (−3%) |
| | 0.5% contaminated | +14 (+22%)* |
| | 0.25% contaminated | −2 (−4%) |
| | 0.25% pure | +4 (+7%) |
| 0.5% substantially pure apraclonidine | Acetone (vehicle) | −5 (−11%) |
| | 0.5% pure | −1 (−3%) |
| | 0.25% pure | −3 (−6%) |
| Oxazolone | oxazolone | +90 (+175%)* |

*$p < 0.01$, Paired T−test

The data reflect positive delayed type hypersensitivity responses to contaminated apraclonidine, but essentially no response to the substantially pure apraclonidine.

EXAMPLE 4

Mice were sensitized as described in Example 3 (at least 20/group). The results are shown in FIG. 1. After 24 doses of pure apraclonidine over an eight week period, the mortality was less than 20%. The mice which were dosed with contaminated apraclonidine had about a 30% mortality rate. The mice which are still being dosed with II are exhibiting a mortality rate of over 50% after 18 doses over 6 weeks. It is expected that the mortality rate will increase over the eight weeks of sensitization.

We claim:

1. A topical composition for controlling intraocular pressure, comprising 0.1 to 10.0 weight percent of (2-[(4-amino-2,6-dichlorophenyl)imino]imidazolidine monohydrochloride substantially free of (2-[(4-amino-2,3,6-trichlorophenyl)imino]imidazolidine in a pharmaceutically acceptable carrier.

2. A method for controlling elevated intraocular pressure in a person suffering therefrom, which comprises administering topically to the eye a composition comprising 0.1 to 10.0 weight percent of (2-[(4-amino-2,6-dichlorophenyl)imino]imidazolidine monohydrochloride substantially free of (2-[(4-amino-2,3,6-trichlorophenyl)imino]imidazolidine in a pharmaceutically acceptable carrier.

3. The method of claim 2 wherein the elevated intraocular pressure is a result of ophthalmic surgery.

4. That method of claim 2 wherein the elevated intraocular pressure is a result of the person suffering from glaucoma or ocular hypertension.

* * * * *